(12) United States Patent
Pantke et al.

(10) Patent No.: US 11,226,002 B2
(45) Date of Patent: Jan. 18, 2022

(54) MAGNETIC BEARING AND METHOD FOR OPERATING A MAGNETIC BEARING

(71) Applicants: THYSSENKRUPP ROTHE ERDE GMBH, Dortmund (DE); thyssenkrupp AG, Essen (DE)

(72) Inventors: Klaus Pantke, Arnsberg (DE); Christopher Stenzel, Soest (DE)

(73) Assignees: THYSSENKRUPP ROTHE ERDE GMBH, Dortmund (DE); THYSSENKRUPP AG, Essen (DE)

( * ) Notice: Subject to any disclaimer, the term of this patent is extended or adjusted under 35 U.S.C. 154(b) by 249 days.

(21) Appl. No.: 16/483,864

(22) PCT Filed: Feb. 15, 2018

(86) PCT No.: PCT/EP2018/053818
§ 371 (c)(1),
(2) Date: Aug. 6, 2019

(87) PCT Pub. No.: WO2018/149932
PCT Pub. Date: Aug. 23, 2018

(65) Prior Publication Data
US 2020/0011376 A1 Jan. 9, 2020

(30) Foreign Application Priority Data
Feb. 17, 2017 (DE) .................. 10 2017 103 332.7

(51) Int. Cl.
*F16C 32/04* (2006.01)
*A61B 6/03* (2006.01)
*H02K 7/09* (2006.01)

(52) U.S. Cl.
CPC .......... *F16C 32/0491* (2013.01); *A61B 6/035* (2013.01); *F16C 32/047* (2013.01); *H02K 7/09* (2013.01); *F16C 2316/10* (2013.01)

(58) Field of Classification Search
CPC F16C 32/0491; F16C 32/047; F16C 32/0442; F16C 2316/10; F16C 32/0468;
(Continued)

(56) References Cited

U.S. PATENT DOCUMENTS

| 4,370,004 A | 1/1983 | Morikawa |
| 5,010,722 A | 4/1991 | Yamaguchi |

(Continued)

FOREIGN PATENT DOCUMENTS

| CN | 202326729 U | 7/2012 |
| CN | 105134779 A | 12/2015 |

(Continued)

OTHER PUBLICATIONS

English Translation of International Search Report issued in PCT/EP2018/053818, dated May 28, 2018.

*Primary Examiner* — Ahmed Elnakib
(74) *Attorney, Agent, or Firm* — thyssenkrupp North America, LLC

(57) ABSTRACT

A magnetic bearing having a first bearing ring and a second bearing ring arranged concentrically in relation to the first bearing ring. The first bearing ring and the second bearing ring are mounted so as to be rotatable with respect to each other about an axis of rotation by means of electromagnets. The first bearing ring has a first magnet row and a second magnet row. The magnet rows each include electromagnets arranged at a distance from one another in a circumferential direction of the first bearing ring. The electromagnets of the magnet rows are oriented such that they can each exert a magnetic force on the second bearing ring, which magnetic force is oriented transversely to the axis of rotation and transversely to a radial plane which is arranged perpendicularly to the axis of rotation.

20 Claims, 8 Drawing Sheets

(58) Field of Classification Search
CPC .. F16C 17/105; F16C 32/0474; F16C 32/048; F16C 2300/14; F16C 32/044; A61B 6/035; H02K 7/09
USPC ........................................................ 310/90.5
See application file for complete search history.

(56) References Cited

U.S. PATENT DOCUMENTS

| | | | |
|---|---|---|---|
| 5,109,659 | A | 5/1992 | Tsuzuki |
| 5,740,666 | A * | 4/1998 | Yamaguchi ............. D01H 7/58 57/100 |
| 6,359,357 | B1 * | 3/2002 | Blumenstock ...... F16C 32/0465 310/90.5 |
| 6,885,121 | B2 * | 4/2005 | Okada ................. F16C 32/0444 310/90.5 |
| 2003/0106384 | A1 | 6/2003 | Yokota |
| 2004/0189125 | A1 * | 9/2004 | Doemen ................. F16C 17/08 310/90.5 |
| 2008/0042504 | A1 | 2/2008 | Thibodeau |
| 2008/0118344 | A1 | 5/2008 | Matsumori |
| 2009/0003746 | A1 | 1/2009 | Norimatsu |
| 2015/0279496 | A1 * | 10/2015 | Bauer .................. A61B 6/4435 378/19 |
| 2016/0053805 | A1 | 2/2016 | Hubert |
| 2016/0091018 | A1 | 3/2016 | Ciulla |

FOREIGN PATENT DOCUMENTS

| | | |
|---|---|---|
| CN | 105378308 A | 3/2016 |
| CN | 105465179 A | 4/2016 |
| DE | 689 24 691 | 4/1996 |
| DE | 10 2008 017 984 A | 10/2009 |
| DE | 10 2014 214 511 A | 1/2016 |
| DE | 10 2015 108 081 A | 11/2016 |
| FR | 2 132 911 | 11/1972 |
| JP | H0369820 A | 3/1991 |
| JP | H08326530 | * 12/1996 |
| JP | H08326530 A | 12/1996 |
| JP | H11 37155 A | 2/1999 |
| JP | H1137155 | * 2/1999 |
| JP | 2000161359 A | 6/2000 |
| KR | 20110092586 A | 8/2011 |

* cited by examiner

MAGNETIC BEARING AND METHOD FOR OPERATING A MAGNETIC BEARING

CROSS REFERENCE TO RELATED APPLICATIONS

This application is a U.S. National Stage Entry of International Patent Application Serial Number PCT/EP2018/053818, filed Feb. 15, 2018, which claims priority to German Patent Application No. DE 10 2017 103 332.7, filed Feb. 17, 2017, the entire contents of both of which are incorporated herein by reference.

FIELD

The present disclosure generally relates to a magnetic bearing and an X-ray computed tomography device.

BACKGROUND

Magnetic bearings are employed for the contactless bearing support of mutually rotatable mechanical elements and, in comparison with rolling bearings or plain bearings, provide an advantage in that exceptionally high speeds of rotation can be achieved. Moreover, magnetic bearings permit virtually noise-free operation.

A magnetic bearing of the above-mentioned type is known, for example, from DE 10 2015 108 081 A1. This magnetic bearing comprises an inner ring and an outer ring, which are mounted so as to be mutually rotatable about an axis of rotation. In the inner ring, a total of three magnet rows are provided, each of which is comprised of a plurality of electromagnets which are configured in a mutually spaced arrangement in the circumferential direction of the inner ring. The electromagnets of a first magnet row are arranged such that they exert a magnetic force on the outer ring, which acts in a radial direction. These electromagnets constitute a radial sectional magnetic bearing. The electromagnets in the other two magnet rows are arranged such they exert magnetic forces on the outer ring in an axial direction. These electromagnets thus constitute axial sectional magnetic bearings.

Known magnetic bearings are entirely proven in practice. However, it has proved to be disadvantageous that a large number of electromagnets is involved, thereby resulting in high production costs.

Thus a need exists for the production of a magnetic bearing with reduced costs.

DETAILED DESCRIPTION

Figure 1:
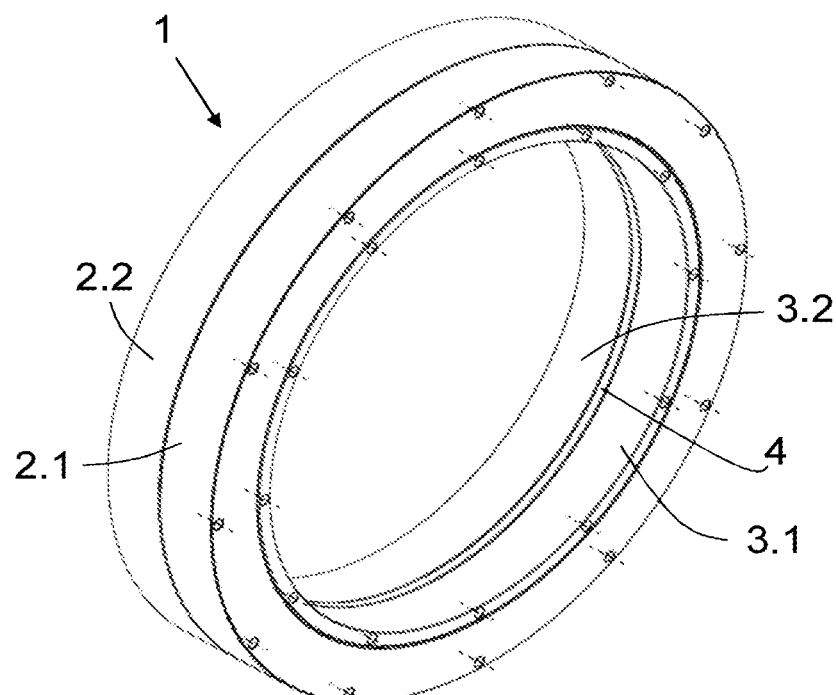
FIG. 1 is a perspective view of a first exemplary embodiment of a magnetic bearing.
Figure 2:
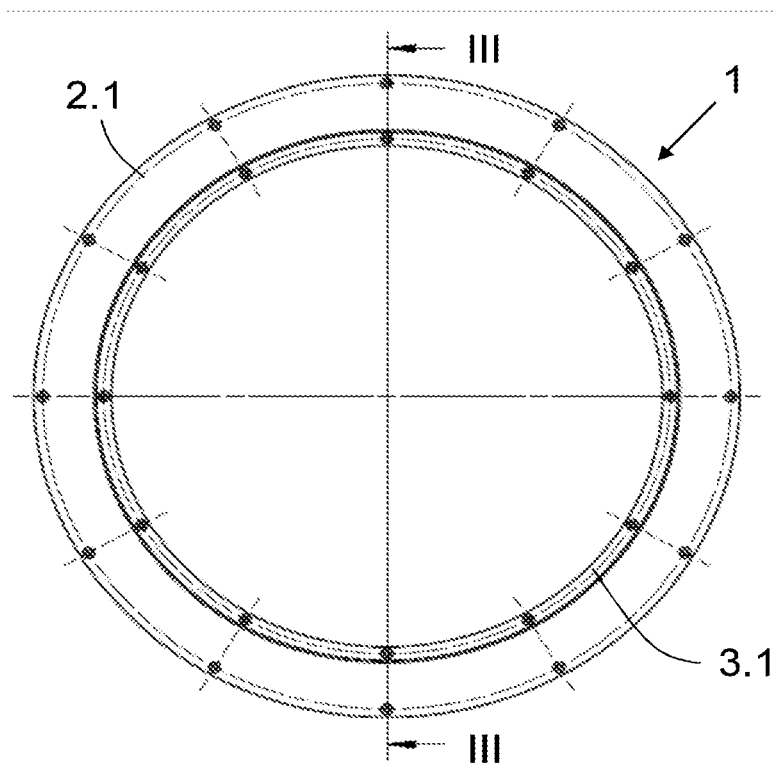
FIG. 2 is a side view of the first exemplary embodiment of the magnetic bearing.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present invention relates to a magnetic bearing having a first bearing ring and a second bearing ring which is arranged concentrically in relation to the first bearing ring, wherein the first bearing ring and the second bearing ring are mounted so as to be rotatable with respect to each other about an axis of rotation by means of electromagnets, wherein the first bearing ring comprises a first magnet row and a second magnet row, wherein the magnet rows each comprise electromagnets arranged at a distance from one another in a circumferential direction of the first bearing ring. A further object of the invention is an X-ray computed tomography device. The invention further relates to a method for the operation of such a magnetic bearing.

In some examples, a magnetic bearing having a first bearing ring and a second bearing ring, which is arranged concentrically in relation to the first bearing ring, wherein the first bearing ring and the second bearing ring are mounted so as to be rotatable with respect to each other about an axis of rotation by means of electromagnets, wherein the first bearing ring comprises a first magnet row and a second magnet row, wherein the magnet rows each comprise electromagnets arranged at a distance from one another in a circumferential direction of the first bearing ring, wherein the electromagnets of the magnet rows are oriented such that they can each exert a magnetic force on the second bearing ring, which magnetic force is oriented transversely to the axis of rotation and transversely to a radial plane which is arranged perpendicularly to the axis of rotation.

The electromagnets of the first and second magnet rows of the magnetic bearing according to the invention are arranged such that they can exert a magnetic force on the second bearing ring, in particular on the working surfaces of the second bearing ring, which comprises force components acting in both the axial direction and the radial direction. By this arrangement, it is possible to constitute a magnetic bearing having only two magnet rows. A third magnet row is not necessary, such that costs for electromagnets in magnetic bearings can be reduced. Moreover, in the first bearing ring, a smaller number of cut-outs for electromagnets can be provided, thereby additionally reducing production costs.

According to a preferred configuration, the magnetic bearing, other than the electromagnets of the first magnet row and the second magnet row, comprises no further electromagnets, such that a particularly cost-effective configuration is provided.

It is constructionally advantageous if the magnetic bearing is configured without permanent magnets. The action of magnetic force on the second bearing ring can then originate exclusively from the electromagnets.

According to a preferred configuration, the electromagnets of the magnet rows respectively comprise a coil, which is wound about a coil core, having a longitudinal axis which lies in the direction of an air gap between the first and the second bearing ring, wherein the longitudinal axis of the coil core is oriented transversely to the axis of rotation and transversely to the radial plane. An arrangement of electromagnets of this type permits a compact configuration. The coil core is preferably configured integrally with the first bearing ring. Alternatively, it is possible for the coil core to be detachably connected to the first bearing ring, for example by means of a screw connection. The coil core can be configured as a pole shoe, by means of which the magnetic field of the coil is directed into the air gap between the first and the second bearing ring. The pole shoe preferably has a curved surface, which is adapted to the curvature of the first bearing ring.

According to an advantageous configuration, the electromagnets of the magnet rows are oriented such that a notional extension of the longitudinal axis of the coil core of an electromagnet in the first magnet row, originating from the first bearing ring in the direction of the second bearing ring, and a notional extension of the longitudinal axis of the coil core of an electromagnet in the second magnet row, originating from the first bearing ring in the direction of the second bearing ring, intersect with a radial plane which is arranged between the first and the second magnet row. An arrangement of this type has proved to be advantageous, in particular for such applications, wherein the magnetic bearing is exposed to symmetrical loading with respect to a radial mid-plane.

According to an alternative advantageous configuration, the electromagnets of the magnet rows are oriented such that a notional extension of the longitudinal axis of the coil core of an electromagnet in the first magnet row, originating from the first bearing ring and extending away from the second bearing ring, and a notional extension of the longitudinal axis of the coil core of an electromagnet in the second magnet row, originating from the first bearing ring and extending away from the second bearing ring, intersect with a radial plane which is arranged between the first and the second magnet row. In comparison with an arrangement of electromagnets wherein the respective extensions, originating from the first bearing ring in the direction of the second bearing ring, intersect with a radial plane between the two magnet rows, this arrangement of electromagnets permits the improved accommodation of torque, and thus provides a more stable bearing.

The second bearing ring preferably comprises working surfaces, on which the magnetic forces of the electromagnets arranged on the first bearing ring act, wherein the working surfaces are arranged transversely to the axis of rotation and transversely to the radial plane. A particularly compact configuration of the magnetic bearing can be achieved, if the second bearing ring assumes an essentially triangular cross-section or an essentially V-shaped cross-section along an axial section plane. The working surfaces of the second bearing ring are preferably arranged such that the normal surface vectors of the working surfaces mutually enclose an angle within the range of 5° to 175°, preferably within the range of 30° to 150°, and particularly preferably within the range of 40° to 140°, or within the range of 45° to 135°, or within the range of 50° to 120°, or within the range of 80° to 100°, for example 90°.

A configuration is preferred in which the electromagnets of the first magnet row, with respect to a radial plane, are arranged symmetrically to the electromagnets of the second magnet row. For example, the electromagnets of the first magnet row can assume the same quantitative inclination vis-à-vis the radial plane. In this manner, it can be achieved that the magnetic forces acting on the second bearing ring are essentially symmetrical with respect to the radial plane. The magnitude of an angle of inclination of the electromagnets of the first and the second magnet row with respect to the radial plane, in particular of the coil cores of the electromagnets of the first and the second magnet row with respect to the radial plane, can lie within the range of 5° to 85°, preferably within the range of 15° to 75°, and particularly preferably within the range of 30° to 60°, for example at an angle of 45°.

Alternatively, the electromagnets of the first magnet row, with respect to a radial plane, can be arranged asymmetrically to the electromagnets of the second magnet row. For example, the electromagnets of the first magnet row, with respect to the radial plane, can assume an offset in relation to the electromagnets of the second magnet row such that, in the circumferential direction of the magnetic bearing, the arrangement of an electromagnet in the first row is offset between two electromagnets in the second magnet row, and vice versa. Alternatively or additionally, an asymmetrical arrangement with respect to a radial plane can be achieved, wherein the electromagnets of the first magnet row and the second magnet row, in particular the coil cores of the electromagnets of the first magnet row and the coil cores of the second magnet row, assume different quantitative inclinations vis-à-vis the radial plane. The magnetic bearing can be adapted to an asymmetrical load situation accordingly. For example, the electromagnets of the first magnet row can assume a larger angle in relation to a radial plane, in order to permit the increased accommodation of axial loads, and the electromagnets of the second magnet row can assume a smaller angle in relation to the radial plane, in order to permit the increased accommodation of radial loads. An angular difference between the angle of inclination of the electromagnets of the first magnet row in relation to the radial plane and the angle of inclination of the electromagnets of the second magnet row in relation to the radial plane preferably lies within the range of 1° to 30°, particularly preferably within the range of 1° to 15°, and particularly preferably within the range of 1° to 10°, for example within the range of 1° to 5°.

It has been established as advantageous if the electromagnets of the first magnet row and the electromagnets of the second magnet row are of a differing design. By means of electromagnets of differing design in the first and the second magnet row, the adaptation of electromagnets to asymmetrical load situations can be simplified. In this manner, a magnetic bearing can be obtained, wherein the magnetic bearing forces of the first and the second magnet row are configured to different strengths. For example, the electromagnets of the first and the second magnet row can assume different numbers of turns, a different coil size and/or a different coil core size. For example, the electromagnets of the first and the second magnet rows can assume a different width and/or a different height and/or a different length. It is advantageous if the ratio of the width and/or height and/or length of the electromagnets of the first and the second magnet row lies within the range of 0.1 to 0.9, preferably within the range of 0.2 to 0.5, particularly preferably within the range of 0.3 to 0.4. Preferably, the electromagnets of the first and the second magnet row differ with respect to the dimensioning of their pole shoes. Alternatively, it is possible for the electromagnets of the first magnet row and the electromagnets of the second magnet row to be of an identical design.

According to an advantageous configuration of the invention, the second bearing ring comprises a flux separator of a non-magnetic material. By means of the flux separator, magnetic circuits generated by the electromagnets of the first and the second magnet rows can be mutually decoupled. It is thus possible for the magnetic forces generated by the electromagnets of the first magnet row and the electromagnets of the second magnet row to be set in an essentially mutually independent manner. The flux separator is preferably configured to an annular design, for example in the form of an annular flux separator element. The flux separator can be arranged in the region between the first magnet row and the second magnet row. The non-magnetic material of the flux separator can be aluminum, austenitic steel, bronze or a ceramic material.

It is advantageous if the magnetic bearing comprises at least one back-up bearing, which is configured as a plain bearing. By means of the back-up bearing, the respectively rotating bearing ring can be captured in the event of the loss of the electric power supply to the electromagnets, with no resulting risk of the mechanical destruction of the bearing. The back-up bearing can comprise a first back-up bearing part, which is arranged on the first bearing ring, and a second back-up bearing part, which is arranged on the second bearing ring. Preferably, the first back-up bearing part is integrated in the first bearing ring and/or the second back-up bearing part is integrated in the second bearing ring.

In this regard, it has proved to be advantageous if the back-up bearing is arranged between the first and the second magnet row. By means of a first back-up bearing arranged between the first and the second magnet row, the magnetic bearing can be captured, without the necessity for further back-up bearings. The back-up bearing is thus arranged internally, in particular centrally to an axial direction of primary motion of the magnetic bearing. The back-up bearing arranged between the first and the second magnet row can comprise a back-up bearing part, in particular arranged on the second bearing ring, which is configured of a non-magnetic material, in particular aluminum, austenitic steel, bronze or a ceramic material. It can thus be achieved that the back-up bearing part simultaneously functions as a flux separator.

Alternatively or additionally, the magnetic bearing can comprise a second and third back-up bearing, which are arranged such that the first magnet row and the second magnet row, considered in the direction of the axis of rotation, are arranged between the second and the third back-up bearings. A design can thus be achieved, wherein the back-up bearings, in the axial direction of primary motion, are arranged externally, or the first and second magnet rows are arranged internally, in particular centrally.

According to an advantageous configuration, the first bearing ring is an outer ring and the second bearing ring is an inner ring. The outer ring can be arranged concentrically outside the inner ring. It is possible for the outer ring to be configured in a fixed arrangement, and for the inner ring to be arranged to rotate in relation to the outer ring. Alternatively, the inner ring can be configured in a fixed arrangement, and the outer ring can be arranged to rotate in relation to the inner ring.

According to an alternative advantageous configuration, the first bearing ring is an inner ring and the second bearing ring is an outer ring. The inner ring can be arranged concentrically within the outer ring. In a configuration of this type it is also possible, either for the outer ring to be configured in a fixed arrangement and for the inner ring to be arranged to rotate in relation to the outer ring, or for the inner ring to be configured in a fixed arrangement, and for the outer ring to be arranged to rotate in relation to the inner ring.

The first bearing ring is preferably configured as a sectional bearing ring having a first annular bearing ring part and a second annular bearing ring part. The assembly of the magnetic bearing can be simplified accordingly. The electromagnets can firstly be fitted to the first bearing ring part and the second bearing ring part, before the connection of the first bearing ring part to the second bearing ring part is executed. Optionally, the first bearing ring can comprise further, in particular annular, bearing ring parts.

The second bearing ring is preferably configured as a sectional bearing ring having a third annular bearing ring part and a fourth annular bearing ring part. The second bearing ring can further comprise an annular back-up bearing part, which is arranged between the third bearing ring part and the fourth bearing ring part.

According to a preferred configuration, the second bearing ring comprises a plurality of sheet metal plates, which are mutually electrically insulated, such that the generation of eddy currents in the second bearing ring can be attenuated. It is specifically preferred if the sheet metal plates are mutually electrically insulated in the axial direction. The sheet metal plates can thus be configured as annular mutually electrically insulated sheet metal plates. Alternatively, it is possible for the sheet metal plates to be mutually electrically insulated in a circumferential direction or a radial direction. Alternatively or additionally, the first bearing ring can comprise a plurality of sheet metal plates, which are mutually electrically insulated, in particular in an axial direction, a circumferential direction or a radial direction. The generation of eddy currents in the first bearing ring can be attenuated accordingly.

A configuration has further proved to be advantageous, in which the electromagnets of a magnet row are arranged in a magnet module. The magnet module can be arranged on the first bearing ring. A configuration of this type provides an advantage, in that the magnet module can be prefabricated, and fitted to the first bearing ring thereafter. The magnet module is preferably configured to an annular design. The magnet module can accommodate all the electromagnets of a magnet row. Alternatively, a plurality of magnet modules, each comprising a plurality of electromagnets, in combination, can constitute a magnet row.

The magnetic bearing described above can be employed as an electric drive. Accordingly, by means of the magnetic bearing, an electric motor which is free of rolling bearings and plain bearings can be provided, wherein the mounting of the respectively rotating bearing ring is achieved by magnetic forces alone, in a contactless arrangement. The respective electromagnets of a magnet row can simultaneously generate forces for magnetic mounting and for propulsion. Alternatively, it is possible for the magnet rows to comprise bearing electromagnets, which generate forces for magnetic mounting, and driving electromagnets, which generate forces for propulsion.

A further object of the invention is an X-ray computed tomography device which incorporates the magnetic bearing described above. By means of the magnetic bearing, an X-ray source and/or an X-ray detector can be moveably mounted with respect to an object to be investigated, for example an object or a person.

For the fulfilment of the above-mentioned object, a method is further proposed for operating a magnetic bearing having a first bearing ring and a second bearing ring, which is arranged concentrically in relation to the first bearing ring, wherein the first bearing ring and the second bearing ring are mounted so as to be rotatable with respect to each other about an axis of rotation by means of electromagnets, wherein the first bearing ring has a first magnet row and a second magnet row, wherein the magnet rows each comprise electromagnets arranged at a distance from one another in a circumferential direction of the first bearing ring, wherein the electromagnets of the magnet rows are oriented such that they can each exert a magnetic force on the second bearing ring, which magnetic force is oriented transversely to the axis of rotation and transversely to a radial plane which is arranged perpendicularly to the axis of rotation.

By this method, the same advantages can be achieved as those described above with respect to the magnetic bearing according to the invention.

Moreover, the advantageous characteristics and configurations described with reference to the magnetic bearing can also be employed in the method for operating the magnetic bearing.

FIGS. 1 to 5 represent a first exemplary embodiment of a magnetic bearing 1 according to the invention. The magnetic bearing 1 can be employed in an X-ray computed tomography device for the moveable mounting of an X-ray source and/or an X-ray detector. The magnetic bearing 1 comprises a first bearing ring 2, which is configured as an outer ring. The first bearing ring 2 comprises two bearing ring parts 2.1, 2.2. The bearing ring parts 2.1, 2.2 are configured to an annular design, and can be detachably interconnected, for example by means of a screw connection. The first bearing ring 2 is thus a sectional bearing ring. A second bearing ring 3 is arranged concentrically within the first bearing ring 2. The second bearing ring 3 also comprises two bearing ring parts 3.1, 3.2. These bearing ring parts 3.1, 3.2 are configured to an annular design. Between the bearing ring parts 3.1, 3.2 of the second bearing ring 3, a back-up bearing part 4 is arranged, which will be further described hereinafter. The first bearing ring 2 is thus an outer ring, and the second bearing ring 3 is an inner ring of the magnetic bearing 1.

The two bearing rings 2, 3, by means of electromagnets 13, 14, are arranged so as to be mutually rotatable about an axis of rotation. The electromagnets 13, 14 of this magnetic bearing 1 are arranged in exactly two magnet rows 11, 12. A first magnet row 11 is constituted by the electromagnets 13 represented on the left-hand side of FIG. 3, which are arranged at a distance from one another in the circumferential direction of the first bearing ring 2. The electromagnets 14 represented on the right-hand side of FIG. 3 constitute a second magnet row 12. The electromagnets 14 of the second magnet row 12 are also arranged at a distance from one another in the circumferential direction. The first and the second magnet row 11, 12 can comprise an identical number of electromagnets 13, 14. In the present case, the magnet rows 11, 12 respectively comprise 16 electromagnets 13, 14.

Alternatively, the number of electromagnets 13, 14 per magnet row 11, 12 can be, for example, four, eight, 12, 14, 18, 20, 22 or 24.

Figure 5:
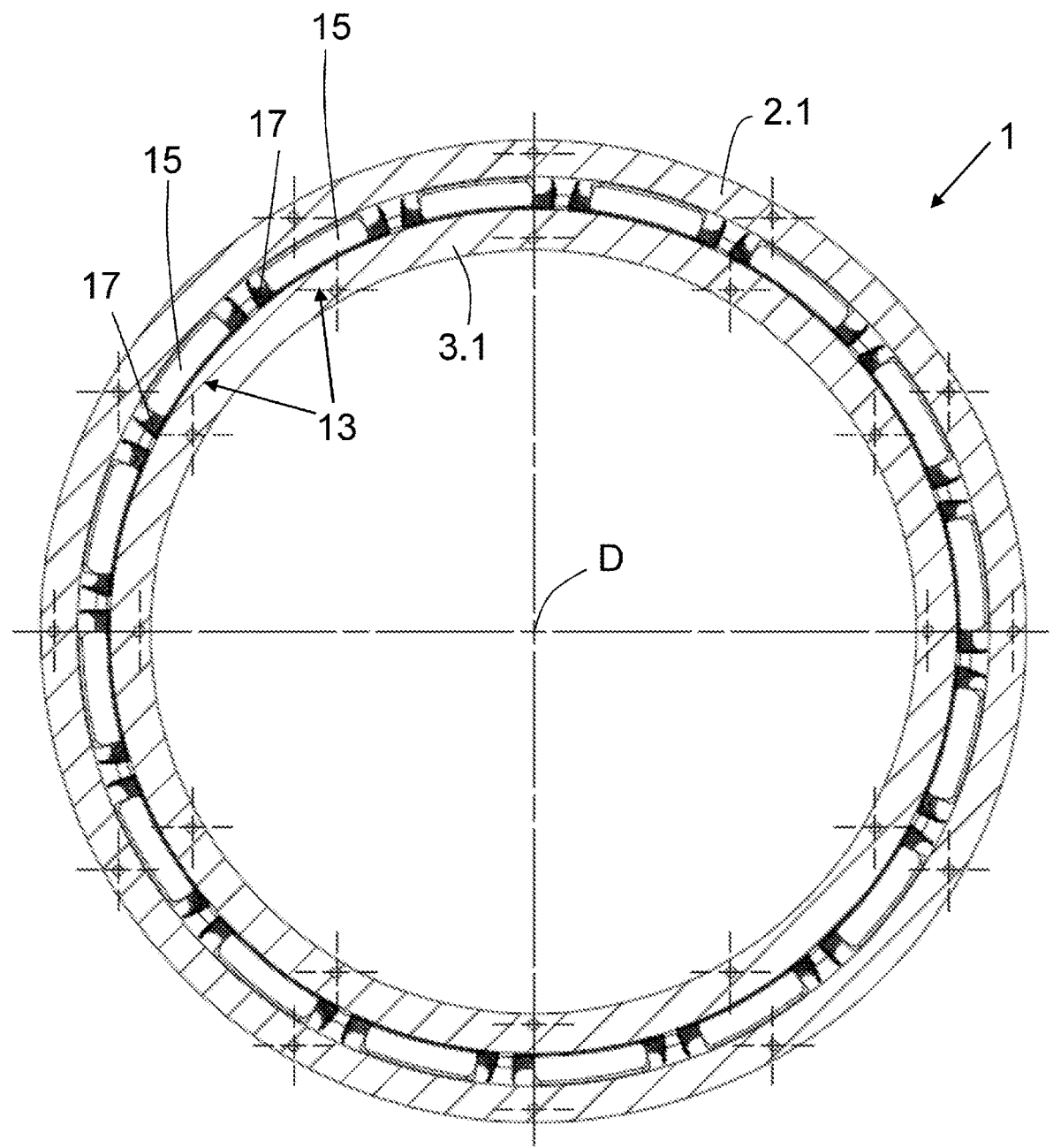
FIG. 5 is a sectional view of the magnetic bearing according to the first exemplary embodiment, along the section plane V-V represented in FIG. 3.
Figure 6:
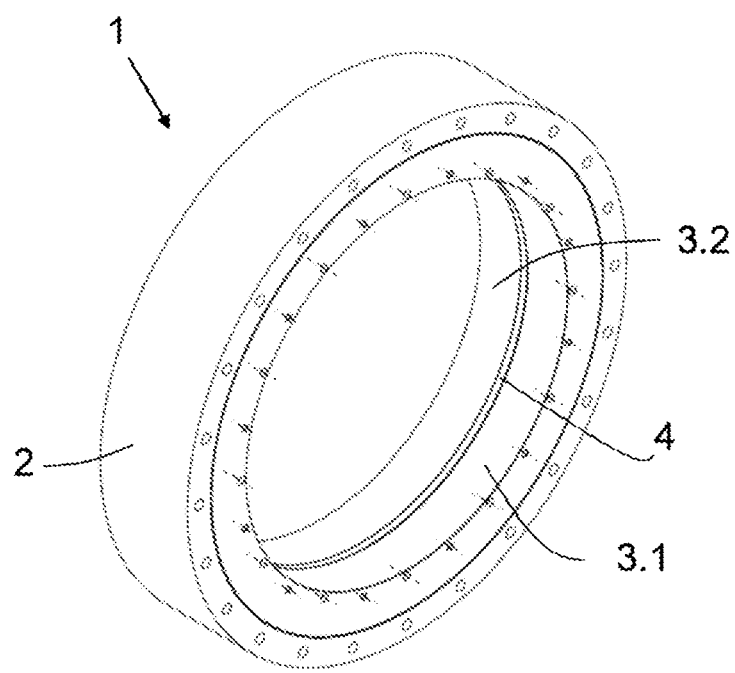
FIG. 6 is a perspective view of a second exemplary embodiment of a magnetic bearing.
Figure 7:
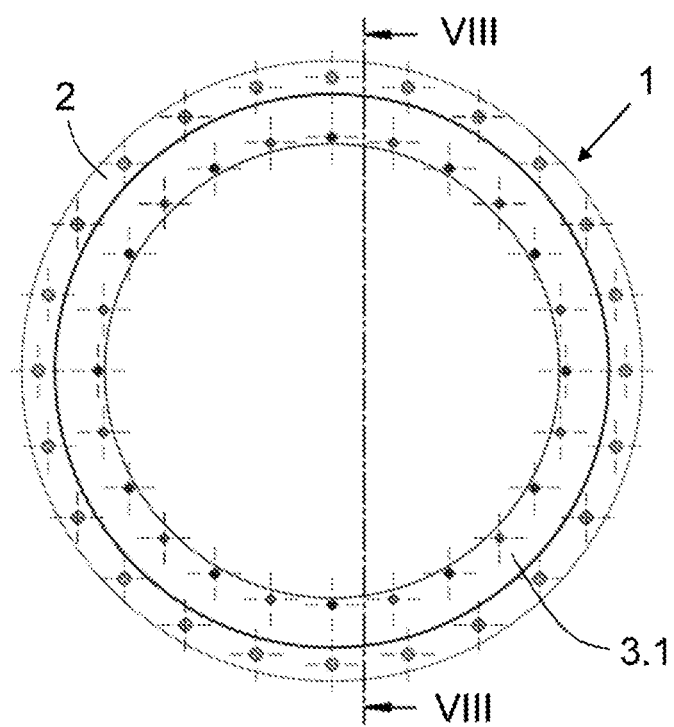
FIG. 7 is a side view of the second exemplary embodiment of the magnetic bearing.
Figure 8:
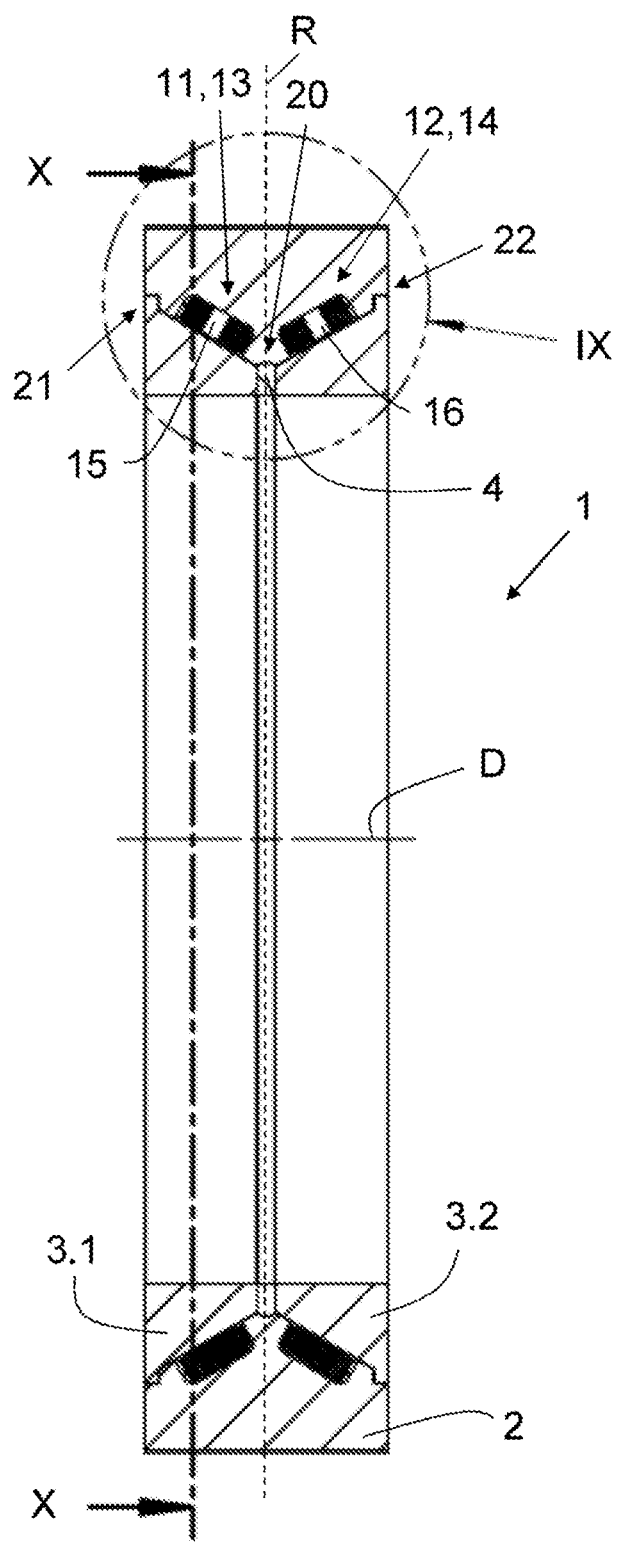
FIG. 8 is a sectional view of the second exemplary embodiment of the magnetic bearing, along the section plane VIII-VIII represented in FIG. 7.

The mutually spaced arrangement of the electromagnets 13 of the first magnet row 11 within the first bearing ring 2 can specifically be seen from the representation shown in FIG. 5. To this end, in the first bearing ring part 2.1 of the first bearing ring 2, one or more cut-outs for the coils 17 of the electromagnets 13 are provided. The coil cores 15 of the electromagnets are preferably configured integrally with the first bearing ring 2, in particular with the first bearing ring part 2.1.

Figure 4:
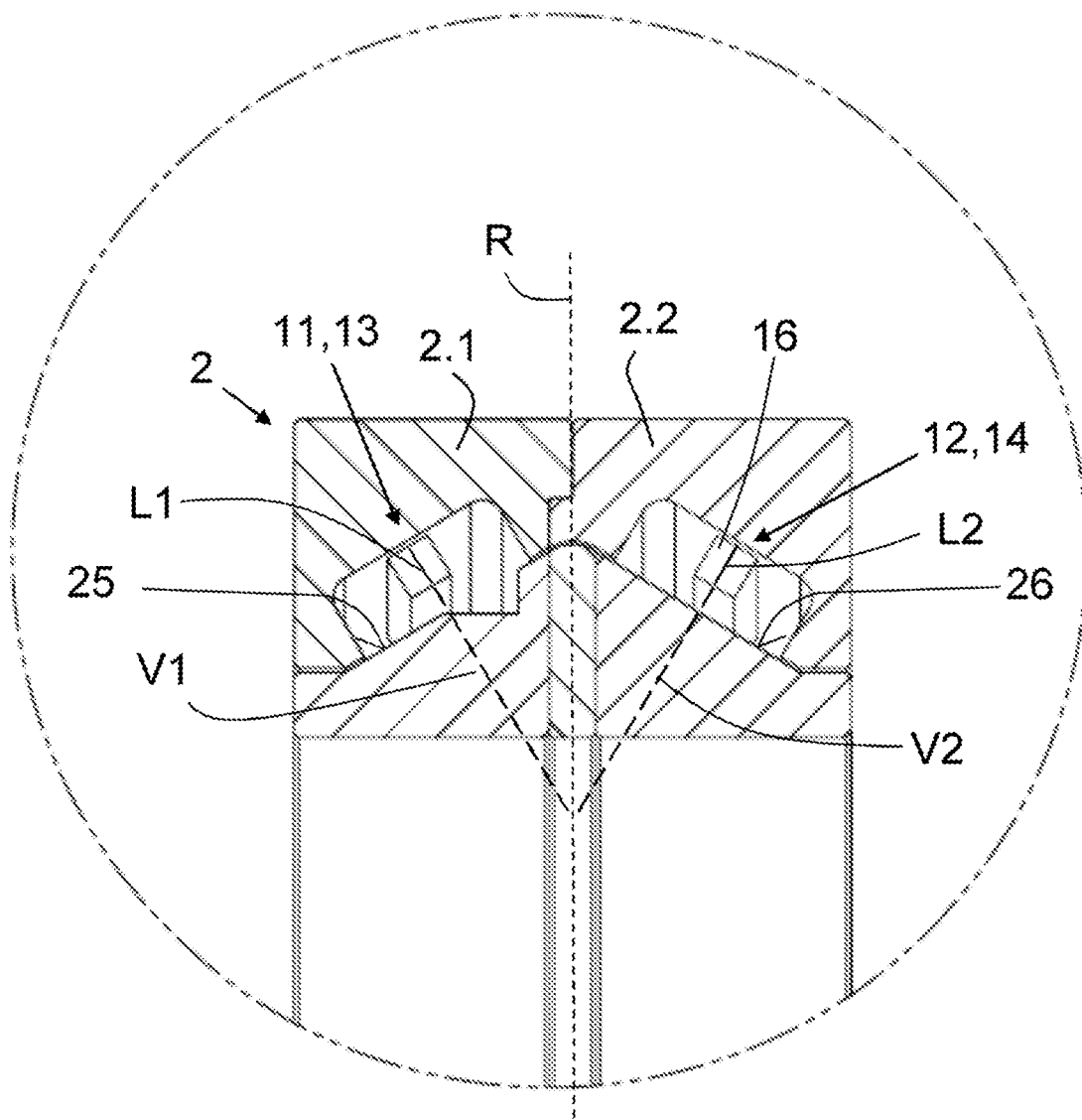
FIG. 4 is a detailed view of the region of the magnetic bearing identified in FIG. 3 by IV.

In the magnetic bearing 1, specific arrangements are adopted in order to permit the most cost-effective manufacture possible. To this end, the electromagnets 13, 14 of the magnet rows 11, 12 are oriented such that they can respectively exert a magnetic force on the second bearing ring 3 which is oriented transversely to the axis of rotation D and transversely to a radial plane R which is arranged perpendicularly to the axis of rotation D. The electromagnets 13, 14 of the first and the second magnet row 11, 12 are thus arranged such that they can exert a magnetic force on the working surfaces 25, 26 provided on the second bearing ring 3 which incorporates force components acting in both an axial direction and in a radial direction—c.f. FIG. 4. These working surfaces 25, 26 are oriented transversely to the axis of rotation D and transversely to the radial plane R. A third magnet row is neither necessary nor provided in the magnetic bearing 1.

Figure 3:
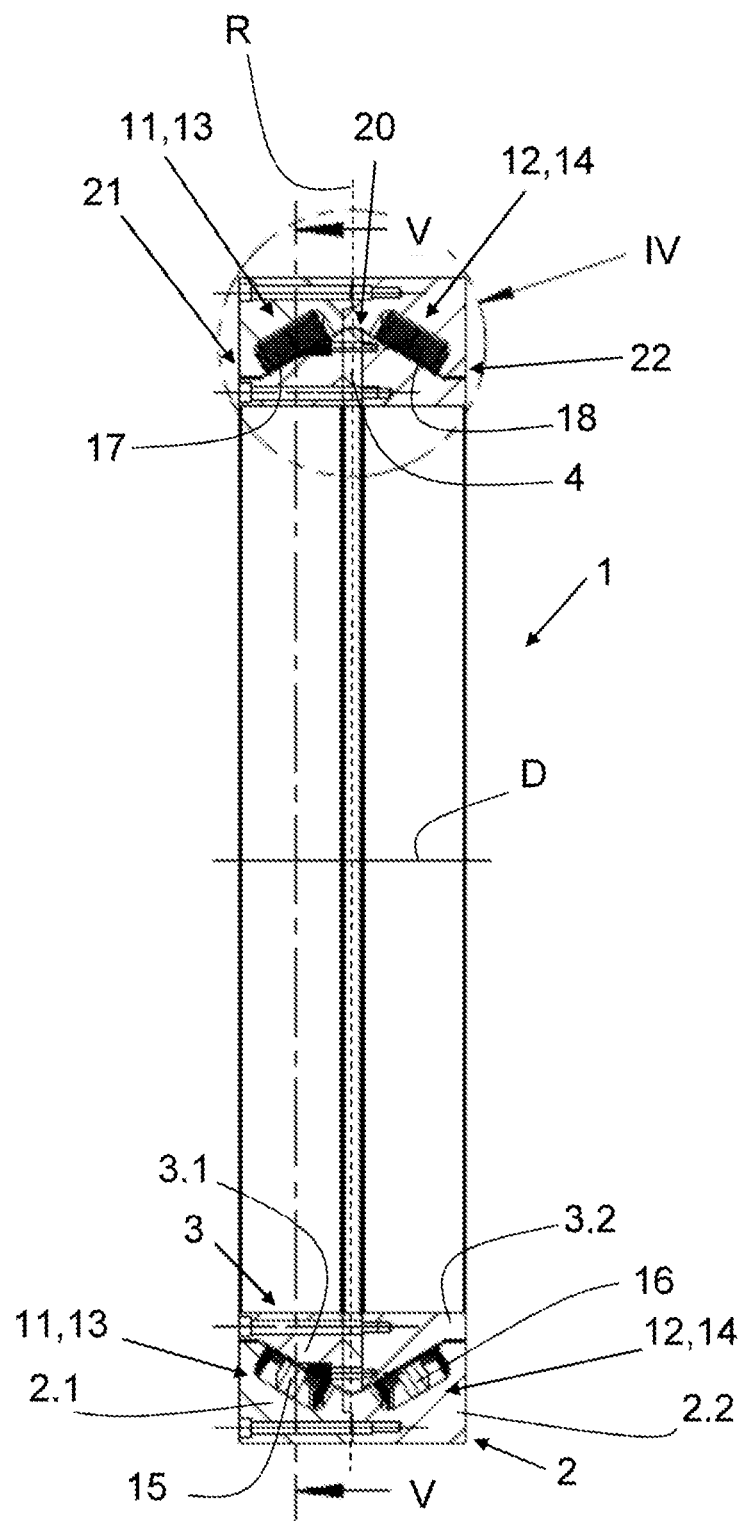
FIG. 3 is a sectional view of the first exemplary embodiment of the magnetic bearing, along the section plane III-III represented in FIG. 2.

As shown in the detailed representation in FIG. 4, the electromagnets 13, 14 of the magnet rows 11, 12 respectively comprise a coil, which is wound about a coil core 15, 16. The coil core 15, 16 respectively has a longitudinal axis L1, L2, which is arranged in the direction of an air gap between the first bearing ring 2 and the second bearing ring 3. The longitudinal axis L1, L2 of the coil core is thus oriented transversely to the axis of rotation D, and transversely to the radial plane R. In the magnetic bearing according to the first exemplary embodiment, the electromagnets 13, 14 of the magnet rows 11, 12 are oriented such that a notional extension V1 of the longitudinal axis L1 of the coil core 15 of an electromagnet 13 in the first magnet row 11, originating from the first bearing ring 2 in the direction of the second bearing ring 3, and a notional extension V2 of the longitudinal axis L2 of the coil core 16 of an electromagnet 14 in the second magnet row 12, originating from the first bearing ring 2 in the direction of the second bearing ring 3, intersect with a radial plane R arranged between the first and the second magnet row. The two extensions V1 and V2 of the longitudinal axes L1, L2 thus converge in the direction of the second bearing ring 3. An essentially triangular cross-section of the second bearing ring 3 is formed along the axial section plane—c.f. FIGS. 3 and 4.

The electromagnets 13 of the first magnet row 11, with respect to the radial plane R, are arranged symmetrically to the electromagnets 14 of the second magnet row 12. The longitudinal axes L1, L2 of the electromagnets 13, 14 can, for example, assume an inclination vis-à-vis the radial plane R, which lies within the range of 5° to 85°, preferably of 15° to 75°, and particularly preferably of 30° to 60°, for example 45°.

The second bearing ring 3 of the magnetic bearing 1 further comprises a flux separator 4 of a non-magnetic material, which is configured to an annular design. The flux separator 4 can be constituted, for example, of aluminum, austenitic steel, bronze or a ceramic material. The flux separator 4, with respect to the magnetic bearing 1, is arranged between the first magnet row 11 and the second magnet row 12, and can thus effectively decouple the magnetic circuits of these two magnet rows 11, 12. The flux separator 4 additionally assumes the function of a back-up bearing 20. To this end, the surface of the flux separator 4 which faces the air gap is configured as a back-up bearing part. A back-up bearing 20, which is configured as a plain bearing, is constituted by the flux separator 4 and the region of the first bearing ring 2 which is arranged opposite the flux separator 4.

Additionally to the first back-up bearing 20, in the magnetic bearing 1 according to the first exemplary embodiment, a second back-up bearing 21 and a third back-up bearing 22 are provided. These back-up bearings 21, 22 are likewise configured as plain bearings, in particular with rounded surfaces. The second back-up bearing 21 and the third back-up bearing 22 are arranged such that the first and the second magnet row 11, 12, considered in the direction of the axis of rotation D, are arranged between the second back-up bearing 21 and a third back-up bearing 22.

FIGS. 6 to 10 represent a second exemplary embodiment of a magnetic bearing 1 according to the invention, which is also suitable for employment in an X-ray computed tomography device. This magnetic bearing 1 comprises a first bearing ring 2, which is configured as an outer ring. The first bearing ring 2 is configured in a one-piece arrangement. Alternatively, the first bearing ring can be configured as a sectional bearing ring. A second bearing ring 3 is arranged concentrically within the first bearing ring 2. The second bearing ring 3 comprises two bearing ring parts 3.1, 3.2. These bearing ring parts 3.1, 3.2 are configured to an annular design. A back-up bearing part 4 is arranged between the bearing ring parts 3.1, 3.2 of the second bearing ring. The second bearing ring 3 is thus a sectional inner ring.

The two bearing rings 2, 3, by means of electromagnets 13, 14, are arranged so as to be mutually rotatable about an axis of rotation. The electromagnets 13, 14 of this magnetic bearing 1 are arranged in exactly two magnet rows 11, 12. A first magnet row 11 is constituted by the electromagnets 13 represented on the left-hand side of FIG. 8, which are arranged at a distance from one another in the circumferential direction of the first bearing ring 2, as can be seen, for example, in FIG. 10. The electromagnets 14 represented on the right-hand side of FIG. 8 constitute a second magnet row 12. The electromagnets 14 of the second magnet row 12 are also arranged at a distance from one another in the circumferential direction. The first and the second magnet row 11, 12 can comprise an identical number of electromagnets 13, 14, for example 16 electromagnets. Alternatively, the number of electromagnets 13, 14 per magnet row 11, 12 can be four, eight, 12, 14, 18, 20, 22, 24 or another value.

Figure 9:
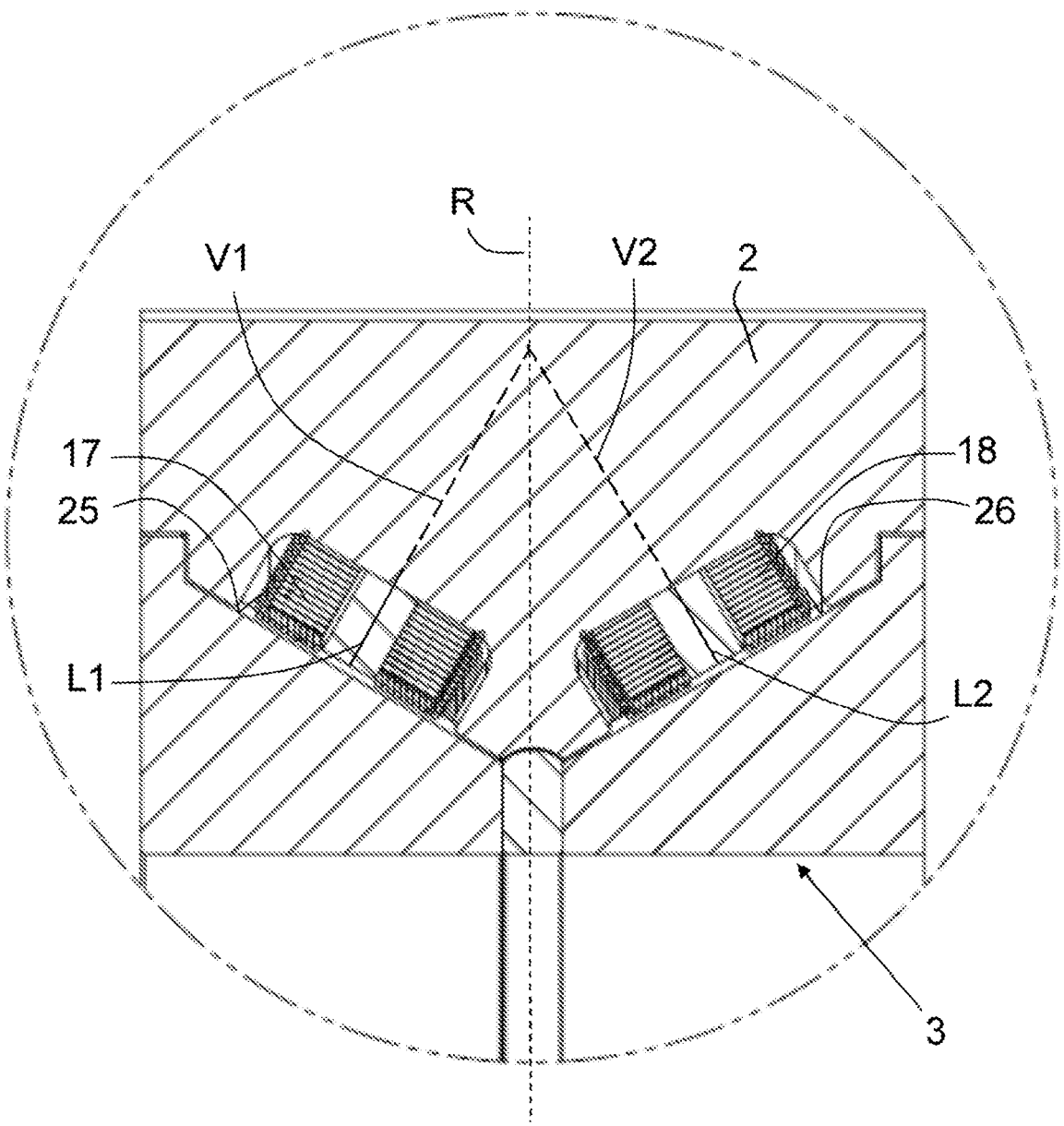
FIG. 9 is a detailed view of the region of the magnetic bearing identified in FIG. 8 by IX.
Figure 10:
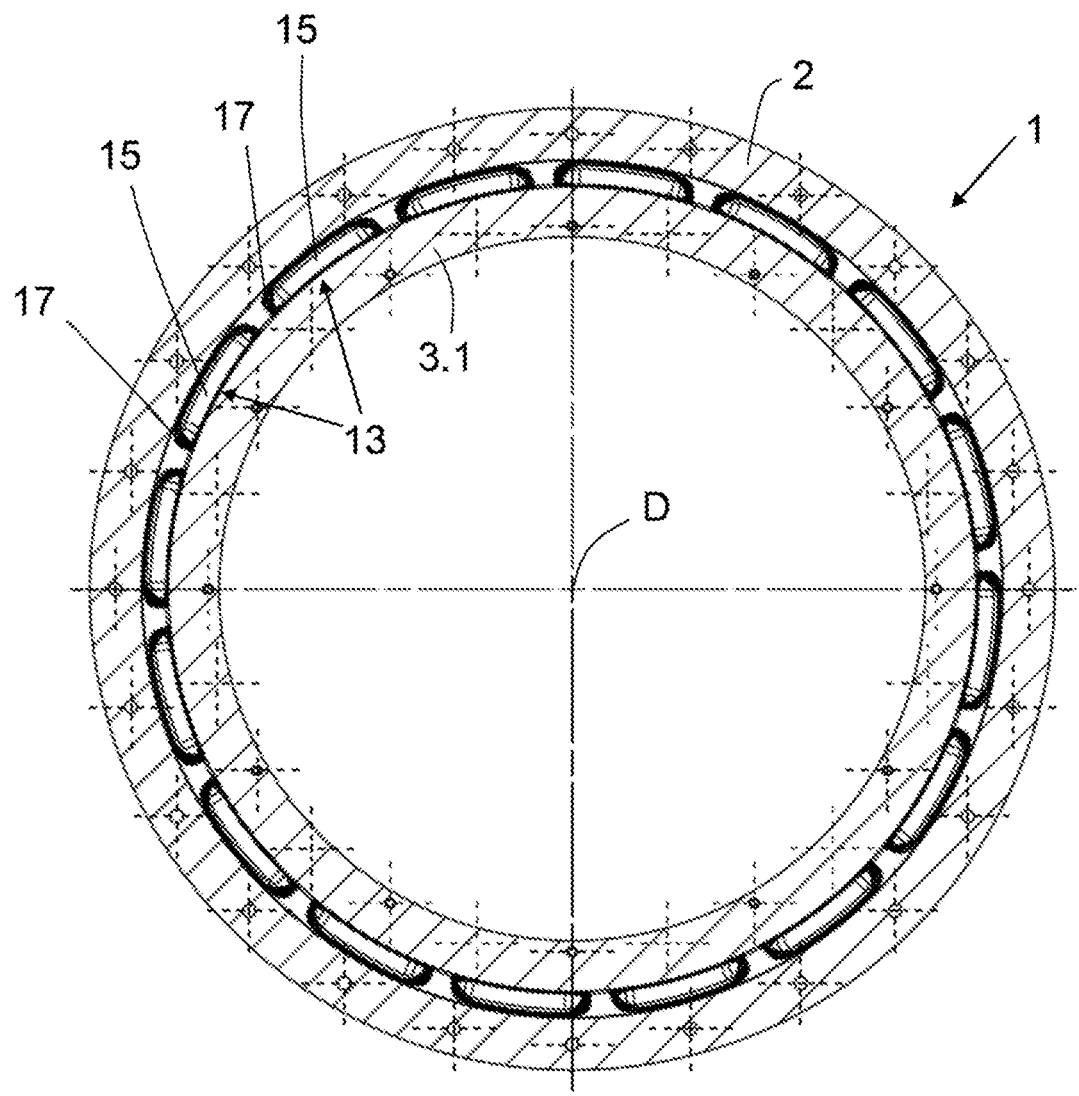
FIG. 10 is a sectional view of the magnetic bearing according to the second exemplary embodiment, along the section plane X-X represented in FIG. 8.

The electromagnets 13, 14 of the magnet rows 11, 12 respectively comprise a coil 17, 18 and a coil core 15, 16. The electromagnets 13, 14 are oriented such that they can respectively exert a magnetic force on the second bearing ring 3 which is oriented transversely to the axis of rotation D and transversely to a radial plane R which is arranged perpendicularly to the axis of rotation D. The electromagnets 13, 14 of the first and the second magnet row 11, 12 are thus arranged such that they can exert a magnetic force on the working surfaces 25, 26 provided on the second bearing ring 3 which incorporates force components acting in both an axial direction and in a radial direction—c.f. FIG. 9. These working surfaces 25, 26 are oriented transversely to the axis of rotation D and transversely to the radial plane R. A third magnet row is neither necessary nor provided in the magnetic bearing 1. The coil core 15, 16 respectively comprises a longitudinal axis L1, L2, which is arranged in the direction of an air gap between the first bearing ring 2 and the second bearing ring 3. The longitudinal axis L1, L2 of the coil core is thus oriented transversely to the axis of rotation D and transversely to the radial plane R.

By way of distinction from the first exemplary embodiment, in the magnetic bearing 1 according to the second exemplary embodiment, the electromagnets 13, 14 of the magnet rows 11, 12 are oriented such that a notional extension V1 of the longitudinal axis L1 of the coil core 15 of an electromagnet 13 in the first magnet row 11, originating from the first bearing ring 2 and extending away from the second bearing ring 3, and a notional extension V2 of the longitudinal axis L2 of the coil core 16 of an electromagnet 14 in the second magnet row 12, originating from the first bearing ring 2 and extending away from the second bearing ring 3, intersect with a radial plane R which is arranged between the first and the second magnet row. The two extensions V1 and V2 of the longitudinal axes L1, L2, which are oriented away from the axis of rotation D, are thus directionally convergent. The working surfaces 25, 26 are arranged on the second bearing ring 3 such that the latter assumes an essentially V-shaped cross-section along an axial section plane.

Similarly to the first exemplary embodiment, the electromagnets 13 of the first magnet row 11, with respect to the radial plane R, are arranged symmetrically to the electromagnets 14 of the second magnet row 12. The longitudinal axes L1, L2 of the electromagnets 13, 14 can, for example, assume an inclination vis-à-vis the radial plane R, which lies within the range of 5° to 85°, preferably of 15° to 75°, and particularly preferably of 30° to 60°, for example 45°.

The second bearing ring 3 of the magnetic bearing 1 further comprises a flux separator 4 of a non-magnetic material, which is configured to an annular design. The flux separator 4 can be constituted, for example, of aluminum, austenitic steel, bronze or a ceramic material. The flux separator 4, with respect to the magnetic bearing 1, is arranged between the first magnet row 11 and the second magnet row 12, and can thus effectively decouple the magnetic circuits of these two magnet rows 11, 12. The flux separator 4 additionally assumes the function of a back-up bearing 20. To this end, the surface of the flux separator 4 which faces the air gap is configured as a back-up bearing part. A back-up bearing 20, which is configured as a plain bearing, is constituted by the flux separator 4 and the region of the first bearing ring 2 which is arranged opposite the flux separator 4. This back-up bearing is located between the first magnet row II and the second magnet row 12.

Additionally to the first back-up bearing 20, in the magnetic bearing 1 according to the second exemplary embodiment, a second back-up bearing 21 and a third back-up bearing 22 are provided. These back-up bearings 21, 22 are likewise configured as plain bearings. The second back-up bearing 21 and the third back-up bearing 22 are arranged such that the first and the second magnet row 11, 12, considered in the direction of the axis of rotation D, are arranged between the second back-up bearing 21 and a third back-up bearing 22.

According to a departure from the exemplary embodiments represented above, the electromagnets 13 of the first magnet row 11 and the electromagnets 12 of the second magnet row 14 can be of a differing design.

The magnetic bearing 1 represented above respectively comprises a first bearing ring 2 and a second bearing ring 3 which is arranged concentrically in relation to the first bearing ring 2, wherein the first bearing ring 2 and the second bearing ring 3 are mounted so as to be rotatable with respect to each other about an axis of rotation D by means of electromagnets 13, 14, wherein the first bearing ring 2 has a first magnet row 11 and a second magnet row 12, wherein the magnet rows 11, 12 each comprise electromagnets 13, 14 arranged at a distance from one another in a circumferential direction of the first bearing ring 2. The electromagnets 13, 14 of the magnet rows 11, 12 are oriented such that they can each exert a magnetic force on the second bearing ring 3, which magnetic force is oriented transversely to the axis of rotation D and transversely to a radial plane R which is arranged perpendicularly to the axis of rotation D.

LIST OF REFERENCE SYMBOLS

1 Magnetic bearing
2 Bearing ring
2.1 Bearing ring part
2.2 Bearing ring part
3 Bearing ring
3.1 Bearing ring part
3.2 Bearing ring part
4 Back-up bearing part
11 Magnet row
12 Magnet row
13 Electromagnet
14 Electromagnet
15 Coil core
16 Coil core
17 Coil
18 Coil
20 Back-up bearing
21 Back-up bearing
22 Back-up bearing
25 Working surface
26 Working surface
D Axis of rotation
L1 Longitudinal axis
L2 Longitudinal axis
R Radial plane
V1 Extension
V2 Extension

What is claimed is:

1. A magnetic bearing, comprising:
a first bearing ring, and
a second bearing ring arranged concentrically with respect to the first bearing ring, the first bearing ring and the second bearing ring mounted so as to be rotatable with respect to each other about an axis of rotation by means of electromagnets,
the first bearing ring comprising a first magnet row and a second magnet row, wherein the magnet rows each comprise electromagnets arranged at a distance from one another in a circumferential direction of the first bearing ring, and the electromagnets of the magnet rows oriented such that they each exert a magnetic force on the second bearing ring, which magnetic force is oriented transversely to the axis of rotation and transversely to a radial plane which is arranged perpendicularly to the axis of rotation,
wherein the second bearing ring comprises an annular flux separator of a non-magnetic material that is configured to function as a back-up bearing.

2. The magnetic bearing of claim 1, wherein the magnetic bearing comprises electromagnets only in the first magnet row and the second magnet row.

3. The magnetic bearing of claim 1, wherein the electromagnets of the magnet rows respectively comprise a coil wound about a coil core, having a longitudinal axis which lies in the direction of an air gap between the first and the second bearing ring, wherein the longitudinal axis of the coil core is oriented transversely to the axis of rotation and transversely to the radial plane.

4. The magnetic bearing of claim 3, wherein the electromagnets of the magnet rows are oriented such that a notional extension of the longitudinal axis of the coil core of an electromagnet in the first magnet row, originating from the first bearing ring in the direction of the second bearing ring, and a notional extension of the longitudinal axis of the coil core of an electromagnet in the second magnet row, originating from the first bearing ring in the direction of the second bearing ring, intersect with a radial plane which is arranged between the first and the second magnet row.

5. The magnetic bearing of claim 3, wherein the electromagnets of the magnet rows are oriented such that a notional extension of the longitudinal axis of the coil core of an electromagnet in the first magnet row, originating from the first bearing ring and extending away from the second bearing ring, and a notional extension of the longitudinal axis of the coil core of an electromagnet in the second magnet row, originating from the first bearing ring and extending away from the second bearing ring, intersect with a radial plane which is arranged between the first and the second magnet row.

6. The magnetic bearing of claim 1, wherein the electromagnets of the first magnet row, with respect to the radial plane, are arranged asymmetrically to the electromagnets of the second magnet row.

7. The magnetic bearing of claim 1, wherein at least one of the following applies with respect to the electromagnets of the first magnet row and the electromagnets of the second magnet row:
the electromagnets of the first magnet row have a different number of turns than the electromagnets of the second magnet row;
the electromagnets of the first magnet row have a different coil size than the electromagnets of the second magnet row;
the electromagnets of the first magnet row have a different coil core size than the electromagnets of the second magnet row;
the electromagnets of the first magnet row have a different width than the electromagnets of the second magnet row;
the electromagnets of the first magnet row have a different height than the electromagnets of the second magnet row;
the electromagnets of the first magnet row have a different length than the electromagnets of the second magnet row; or
the electromagnets of the first magnet row have pole shoes with different dimensions than the electromagnets of the second magnet row.

8. The magnetic bearing of claim 1, wherein the annular flux separator is disposed on a radially-inner side of the second bearing ring.

9. The magnetic bearing of claim 1, wherein the back-up bearing is a back-up plain bearing.

10. The magnetic bearing of claim 9, wherein the back-up bearing is arranged between the first and the second magnet row.

11. The magnetic bearing of claim 9, wherein the first and the second magnet row, considered in the direction of the axis of rotation, is arranged between a second back-up bearing and a third back-up bearing.

12. The magnetic bearing of claim 1, wherein the first bearing ring is an outer ring, and the second bearing ring is an inner ring.

13. The magnetic bearing of claim 1, wherein the first bearing ring is an inner ring, and the second bearing ring is an outer ring.

14. The magnetic bearing of claim 1, wherein the first bearing ring is configured as a sectional bearing ring having a first annular bearing ring part and a second annular bearing ring part.

15. The magnetic bearing of claim 1, wherein the second bearing ring is configured as a sectional bearing ring having a third annular bearing ring part and a fourth annular bearing ring part.

16. The magnetic bearing of claim 1, wherein the first bearing ring and/or the second bearing ring comprises a plurality of sheet metal plates which are mutually electrically insulated.

17. An X-ray computed tomography device, comprising the magnetic bearing of claim 1.

18. The magnetic bearing of claim 1, wherein the annular flux separator is disposed on a radially-inner side of the second bearing ring, wherein the second bearing ring has a length that extends in a direction parallel to the axis of rotation, wherein the annular flux separator is disposed at a midpoint of the length of the second bearing ring.

19. A method for operating a magnetic bearing having a first bearing ring and a second bearing ring arranged concentrically in relation to the first bearing ring, wherein the first bearing ring and the second bearing ring are mounted so as to be rotatable with respect to each other about an axis of rotation by means of electromagnets, wherein the first bearing ring has a first magnet row and a second magnet row, wherein the magnet rows each comprise electromagnets arranged at a distance from one another in a circumferential direction of the first bearing ring, wherein the electromagnets of the magnet rows are oriented to exert a magnetic force on the second bearing ring, which magnetic force is oriented transversely to the axis of rotation and transversely to a radial plane which is arranged perpendicularly to the axis of rotation, wherein the second bearing ring comprises an annular flux separator of a non-magnetic material that is configured to function as a back-up bearing, the method comprising rotating one of the first bearing ring and the second bearing ring relative to the other of the first bearing ring and the second bearing ring.

20. The method of claim 19 wherein the electromagnets of the first magnet row, with respect to the radial plane, are arranged asymmetrically to the electromagnets of the second magnet row.

* * * * *